United States Patent
Yagihashi et al.

(10) Patent No.: US 6,841,334 B2
(45) Date of Patent: Jan. 11, 2005

(54) ONIUM SALTS AND POSITIVE RESIST MATERIALS USING THE SAME

(75) Inventors: Fujio Yagihashi, Yokohama (JP); Tomoyoshi Furihata, Kawasaki (JP); Jun Watanabe, Kawasaki (JP); Akinobu Tanaka, Atsugi (JP); Yoshio Kawai, Isehara (JP); Tadahito Matsuda, Atsugi (JP)

(73) Assignees: Shin-Etsu Chemical Co., Ltd., Tokyo (JP); Nippon Telegraph and Telephone Corporation, Tokyo (JP)

( * ) Notice: Subject to any disclaimer, the term of this patent is extended or adjusted under 35 U.S.C. 154(b) by 0 days.

(21) Appl. No.: 10/683,107

(22) Filed: Oct. 10, 2003

(65) Prior Publication Data

US 2004/0076905 A1 Apr. 22, 2004

Related U.S. Application Data

(62) Division of application No. 08/815,410, filed on Mar. 11, 1997, now abandoned, which is a division of application No. 08/192,903, filed on Feb. 7, 1994, now abandoned.

(30) Foreign Application Priority Data

| Feb. 8, 1993 | (JP) | .............................................. 5-041715 |
| Sep. 2, 1993 | (JP) | .............................................. 5-242101 |

(51) Int. Cl.$^7$ .............................................. G03F 7/038
(52) U.S. Cl. .............................. 430/270.1; 430/286.1; 430/905; 430/914; 522/61; 568/13
(58) Field of Search .......................... 430/270.1, 286.1, 430/905, 914; 522/61; 568/13

(56) References Cited

U.S. PATENT DOCUMENTS

| 2,833,827 A | | 5/1958 | Hahn et al. |
| 3,723,534 A | | 3/1973 | Ratts |
| 4,256,828 A | | 3/1981 | Smith |
| 5,164,278 A | | 11/1992 | Brunsvold et al. |
| 5,220,037 A | | 6/1993 | Schwalm et al. |
| 5,314,929 A | | 5/1994 | Crivello et al. |
| 5,346,803 A | * | 9/1994 | Crivello et al. .......... 430/270.1 |
| 5,580,695 A | | 12/1996 | Murata et al. |
| 5,612,170 A | * | 3/1997 | Takemura et al. ....... 430/270.1 |
| 5,624,787 A | | 4/1997 | Watanabe et al. |
| 5,691,112 A | | 11/1997 | Watanabe et al. |
| 6,613,844 B2 | * | 9/2003 | Watanabe et al. ........... 525/241 |

FOREIGN PATENT DOCUMENTS

| EP | 05-20265 A2 | 12/1992 |
| EP | 523957 A1 | 1/1993 |
| JP | 61-12725 A2 | 1/1986 |
| JP | 63-223002 A2 | 9/1988 |

* cited by examiner

*Primary Examiner*—Yvette C. Thornton
(74) *Attorney, Agent, or Firm*—Millen, White, Zelano, Branigan, P.C.

(57) ABSTRACT

Disclosed are novel onium salts represented by general formula $(R)_3S^+M$, wherein three R's may be the same or different, each being an aryl group, provided that at least one of R's is a t-alkoxy substituted phenyl group, and M is an anion capable of forming the sulfonium salts; and high energy radiation-responsive positive resist materials using said novel onium salts as acid generator.

11 Claims, No Drawings

ONIUM SALTS AND POSITIVE RESIST MATERIALS USING THE SAME

This application is a divisional of U.S. Ser. No. 08/815,410, filed Mar. 11, 1997, now abandoned; Ser. No. 08/815,410 is a divisional of U.S. Ser. No. 08/192,903, filed Feb. 7, 1994, now abandoned.

FIELD OF THE INVENTION

This invention relates to novel onium salts and positive resist materials using the same and, more particularly, to novel onium salts suitable for positive resist materials of the type which are highly sensitive to high energy radiations, such as deep ultraviolet rays (DUV), electron beams and X-rays, developable with an aqueous alkali solution and well suited for fine processing technology, and to positive resist materials using said onium salts.

BACKGROUND OF THE INVENTION

In proportion as large scale integrated circuits (LSI) are heightened in integration level and operation speed, further fining the pattern rules is required. However, the light hitherto used in photoexposure technology contained different wavelengths, and these wavelengths were long. Consequently, there was a limit in fining the pattern rules. Thus, it was tried to use as light source g-line (436 nm) or i-line (365 nm) emitted from an ultrahigh-pressure mercury lamp. Even in those cases, however, the pattern rule limit was about 0.5 $\mu$m with respect to resolution, and the manufacture of LSI utilizing such photoexposure arts can attain at best the integration level corresponding to 16 Mbit DRAM.

In this context, deep ultraviolet (DUV) lithography using as a light source deep ultraviolet rays, which are shorter in wavelength than g-line and i-line, appears to offer promise as a new processing technology.

DUV lithography can achieve 0.1–0.3 $\mu$m resolutions in the imaging process, and can provide a pattern having effectively vertical walls with respect to the substrate if a resist having a low optical absorbance is used. Moreover, as this technology makes it possible to transfer a pattern in one operation, it offers a higher throughput than electron beam lithography.

In recent years, on the other hand, high intensity KrF excimer laser has been successfully used as the light source for DUV lithography. In order that DUV lithography using such a light source has practical utility in mass production of LSI, it is necessary to use resist materials having low optical absorbance and high sensitivity at the wavelength of that laser.

Thus, there have been lately developed the chemical amplification type resist materials which use an acid as a catalyst and possess not only sensitivities equivalent to or higher than those of conventional high sensitivity resists but also other excellent properties including high resolution and high dry-etching resistance (as proposed, e.g., by Liu et al in *J. Vac. Sci. Technol.*, Vol. B6, p. 379 (1988)). As for the negative resists of the aforementioned type, Shipley Company is already marketing a three-component chemically amplified resist (trade name, SAL601ER7) which consists of a novolak resin, a melamine compound and an acid generator.

When negative resist materials are used in the manufacturing process of LSI, they can serve for wiring and gate forming processes in the LSI production, but it is difficult for them to form contact holes because fine processing techniques are required therein.

On the other hand, hitherto proposed chemically amplified positive resists have a defect such that when they are used without undergoing any modification in forming patterns in accordance with DUV, electron-beam or X-ray lithography the developed patterns tend to overhang in profile because of the lowering of the solubility at the resist surface (K. G. Chiong, et al., J. Vac. Sci. Technol., Vol. B7, (6), p. 1771, (1989)). This overhanging phenomenon is at disadvantage in making the dimensional control of the patterns difficult to result in impairing dimensional controllability in the processing of substrates by the use of a dry etching technique or, what is worse, in readily causing the collapse of the patterns.

Accordingly, there has been a strong demand for developing positive resist materials of chemical amplification type which are free from the above-described defect and have high performance.

In compliance with such a demand, Ito et al have proposed the chemically amplified positive resist material consisting of a resin called PBOCST, or a poly(hydroxystyrene) protected with t-butoxycarbonyl groups, and an onium salt ("Polymers in Electronics", ACS Symposium Series, No. 242, American Chemical Society, Washington, D.C., 1984, p. 11).

However, the onium salt used therein contains antimony as a metal component, so that the substrate is contaminated with the antimony. In addition, the resist material recited above suffers from a very great change with the lapse of time after irradiation with DUV or the like.

Another positive resist material for DUV lithography has been proposed by Ueno et al, wherein poly(p-styreneoxytetrahydropyranyl) is used as the principal component and an acid generator is added thereto (36th Oyoo Butsuri Gakkai Kanren Rengo Koenkai, 1989, 1p-k-7).

The foregoing resist material, however, tends to undergo positive to negative inversion when exposed to deep ultraviolet rays, electron beams or X-rays.

Moreover, with the two-component positive resist materials as recited above, which are constituted of a resin, whose OH groups are protected with certain groups, and an acid generator, it is necessary to decompose many of the protected groups in order to render the resist soluble in a developer. The decomposition involves a considerably high risk of film thickness variations, in-film stress or air bubbles in the process of LSI production.

Such being the case, there have been developed three-component positive resist materials as chemically amplified positive resist systems which are free from defects of the foregoing two-component ones. The three-component resist system consists of an alkali-soluble resin, a dissolution inhibitor and an acid generator.

As a three-component positive resist material, the resist material RAY/PF (produced by Hoechst AG.), which contains a novolak resin, an acetal compound as a dissolution inhibitor and an acid generator, has been developed for X-ray lithography.

However, the resist sensitivity thereof closely depends on the time elapsed from the exposure to X-rays until the development, because the resist material RAY/PF undergoes chemical amplification at room temperature. Accordingly, it is necessary to systematically perform strict control of that time. In actual practice, however, it is not easy to strictly regulate the time between the exposure and developing steps. That material cannot therefore ensure dimensional stability to the patterns formed therein. In addition, it has another disadvantage in that its optical absorbance at the wavelength of KrF excimer laser beam (248 run) is so high that it is unsuitable for the lithography using that laser.

In general, in order to effect chemical amplification, many resist materials require a heat treatment after exposure (the so-called post-exposure baking, abbreviated as "PEB"). Although PEB is an additional processing step, compared with the case in which resist systems undergo chemical amplification at room temperature, it enables less severe regulation of the time between exposure and developing steps. Thus, the resist materials requiring PEB can bear stable resist characteristics.

In a resist system which undergoes hydrolysis in the chemical amplification step, water is required for the hydrolysis reaction, and the resist material must therefore contain an appropriate amount of water.

In many cases, organic solvents immiscible with water, such as ethoxyethyl acetate, are used as a solvent for coating a resist material on a substrate, and resins which themselves are not compatible with water are used as a constituent of resist materials. Under these circumstances, it is difficult to incorporate a predetermined amount of water in such resist materials, and even if water can be incorporated therein, it will be troublesome to control the water content.

On the other hand, the decomposition reaction of t-butoxycarbonyloxy group does not require any water. More specifically, two components alone, namely, t-butoxycarbonyloxy group and an acid as catalyst, take part in the progress of the reaction. Therefore, the decomposition reaction is more suitable for chemical amplification.

Moreover, many of the t-butoxycarbonyloxy containing compounds are known to inhibit the dissolution of novolak resins, which infers that t-butoxycarbonyloxy group has dissolution inhibiting effect on novolak resins.

Taking into account the knowledge described above, Schlegel et al have reported a three-component positive resist material consisting of a novolak resin, t-butoxycarbonyl protected bisphenol A as dissolution inhibitor and pyrogallol methanesulfonic acid ester (37th Oyoo Butsuri Gakkai Kanren Rengo Koenkai, Spring 1990, 28p-ZE-4).

Such a resist material is, however, difficult of practical use, because the novolak resin has high optical absorbance.

Schwalm et al have developed bis(p-t-butoxycarbonyloxyphenyl) iodonium hexafluoroantimonate as a compound in which two functions of the dissolution inhibitor and the acid generator are combined (Polymer for Microelectronics, Tokyo 1989, Session A38), and have reported the mixture of that compound with a novolak resin as a positive resist material for DUV lithography.

However, as the foregoing resist material contains not only the novolak resin having high optical absorbance but also the metal, it is not suitable for practical application.

On the other hand, it is known that in the chemically amplified positive resist materials of three-component type, which are constituted of a resin, a dissolution inhibitor and an acid generator, the acid generator used has a particularly great influence on the performance as a resist material.

Typical examples of such an acid generator include $(C_6H_5)_3S^{+-}O_3SCF_3$, $(C_6H_5)_3S^{+-}PF_6$, $(C_6H_5)_3S^{+-}SbF_6$, $(C_6H_5SC_6H_4)(C_6H_5)_2S^{+-O}{}_3CF_3$, $CH_3OC_6H_5(C_6H_5)_2S^{+-}OSO_2CF_3$, and so on.

Of these acid generators, substituted or unsubstituted triphenylsulfonium compounds have a characteristic such that they are decomposed by irradiation with high energy beams, including ultraviolet rays and electron beams, to produce acids. Thus, these compounds have so far been used widely, e.g., as a photopolymerization initiator in cation polymerization, a photocuring agent for epoxy resins, an acid generator for photoresists, and so on. When hitherto used triphenylsulfonium compounds are incorporated as a constituent of resist materials, they can lower the solubility of the resists in aqueous alkali solutions and further can inhibit the resist film from thinning upon development, because they themselves are soluble in oils.

However, the dissolution speed of those resists in an aqueous alkali solution is lowered in the exposed area also, which corresponds to the space part of the resist pattern, since the decomposition products which the acid generators yield by absorbing high energy beams are also soluble in oils. In such resist materials, it is therefore impossible to enlarge a ratio of the alkali dissolution speed in the area irradiated with high energy beams to that in the area unirradiated therewith (this ratio is generally called "dissolution contrast"). Thus, when developed, the resist materials using the triphenylsulfonium compounds suffer from disadvantages of (1) not securing sufficient sensitivity, (2) providing low resolution, (3) being apt to forming a slightly soluble layer at the resist surface, (4) having insufficient etchability, and so on.

Meantime, acid generators other than the foregoing compounds have some of the disadvantages cited above, too. The resist materials containing them therefore suffer from the lowering of performance.

SUMMARY OF THE INVENTION

As a result of intensive studies on acid generators, we have found out novel onium salts which, when used as acid generator in combination with a resin and a dissolution inhibitor to constitute a chemically amplified positive resist material, can ensure higher performance than ever with respect to sensitivity, resolution and process suitability to the resulting materials in high energy radiation lithography.

That is, a first object of the present invention is to provide novel onium salts suitable for an acid generator of positive resist materials.

A second object of the present invention is to provide positive resist materials for high energy radiation lithography which have higher performance than ever with respect to sensitivity, resolution and process suitability.

The above-described objects are respectively attained with onium salts represented by the following general formula (I) and positive resist materials using said onium salts:

$$(R)_3S^+M \qquad (I)$$

wherein three R's may be the same or different, each being an aryl group, provided that at least one of R's is a t-alkoxy substituted phenyl group; and M is an anion capable of forming the sulfonium salts.

DETAILED DESCRIPTION OF THE INVENTION

In the foregoing general formula (I), the aryl group represented by R includes phenyl, 3-methylphenyl, 4-methylphenyl, 4-isopropylphenyl, 4-t-butylphenyl, 4-fluorophenyl, 3-fluorophenyl, 4-chlorophenyl, 2-methoxyphenyl, 3-methoxyphenyl, 4-methoxyphenyl, 4-phenoxyphenyl, 4-phenylthiophenyl, 3-trifluoromethylphenyl, 4-trifluoromethylphenyl and like groups.

The anion represented by M in general formula (I) may be any anion so far as it is free from a nucleophilic property.

Specific examples of such an anion include hexafluorophosphate, hexafluoroantimonate, hexafluoroarsenate, trifluoromethanesulfonate, paratoluenesulfonate, tetrafluoroborate, fluorosulfonate and like ions. Of these anions, trifluoromethanesulfonate (abbreviated as "triflate" hereinafter) and paratoluene-sulfonate (abbreviated as "tosylate" hereinafter) are favored in particular from the standpoint of avoiding the metal-ion contamination of the resist base.

Of the present onium salts, those represented by the following general formula (II) are particularly preferred:

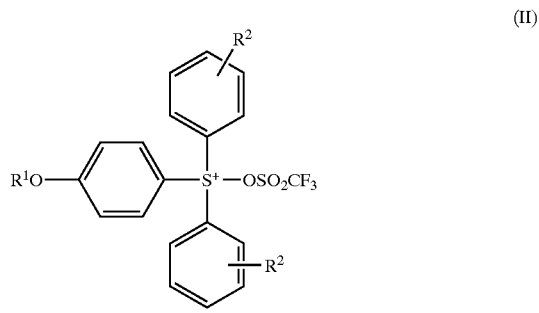

wherein $R^1$ represents a tertiary lower alkyl group, and $R^2$ represents a lower alkyl group or an alkoxy group.

In the foregoing formula, it is preferable that $R^1$ be a t-butyl group and $R^2$ be a methyl, ethyl, methoxy or ethoxy group.

As for the method of preparing a sulfonium salt, there have so far been adopted (1) the method of using aluminum chloride as catalyst, (2) the $P_2O_5$/methanesulfonic acid process, (3) the method of reacting an iodonium salt with a sulfide in the presence of a copper catalyst, and so on. In the foregoing preparation methods (1) and (2), the reactions are carried out under an acidic condition. Thus, the release of a tertiary alkoxy group proceeds therein. It is therefore impossible to obtain the present onium salts in accordance with those methods. The foregoing method (3), on the other hand, requires a high reaction temperature for progress of the reaction. Thus, the reaction contends with the pyrolysis of tertiary alkoxy groups. It is therefore difficult for the method (3) also to provide the intended sulfonium salts.

In contrast with the above-described cases, when there is adopted the method of using a tertiary alkoxy-substituted phenyl Grignard reagent obtained from a quaternary alkoxy-substituted phenyl halide and reacting said reagent with various sulfoxides, preferably in the presence of trimethyl-silyl triflate (or trimethylsilyl trifluoromethane sulfonate), the novel onium salts of the present invention can be obtained in a high yield.

Then, taking up a tertiary butoxy-substituted triphenyl-sulfonium salt as specific example, the method adopted in preparing the present onium salts is illustrated below in detail.

A tertiary butoxy-substituted triphenylsulfonium salt can be prepared by allowing tertiary butoxy-substituted phenyl Grignard reagent to react with a substituted or unsubstituted diphenylsulfoxide, preferably in the presence of trimethyl-silyl triflate. Additionally, the foregoing tertiary butoxy-substituted Grignard reagent can be easily prepared, e.g., using metallic magnesium, tetrahydrofuran and tertiary butoxy-substituted bromobenzene in accordance with a known method.

Specific examples of a substituted diphenylsulfoxide which can be used include p-methylphenylsulfoxide, p-t-butylphenylsulfoxide, p-methoxyphenylsulfoxide, and the like.

In the preparation reaction, it is desirable that the substituted or unsubstituted diphenylsulfoxide and the tertiary butoxy-substituted phenyl Grignard reagent be used in a ratio of 1:0.8 to 1:1.2 by mole, and trimethylsilyl triflate be used in an amount equimolar to the Grignard reagent.

The reaction process comprises, in succession, cooling, e.g., diphenylsulfoxide dissolved in methylene chloride to a temperature ranging from $-30°$ C. to $-70°$ C., stirring the solution while keeping it at a temperature below $-30°$ C., thereto adding dropwise trimethylsilyl triflate, raising the temperature of the thus obtained solution up to $0\sim10°$ C., allowing it to stand for about 30 minutes, cooling it again down to $-30\sim-70°$ C., thereto adding dropwise tertiary butoxy-substituted phenyl Grignard reagent while keeping the resulting solution at a temperature below $-30°$ C., raising the temperature of the mixture up to $0\sim10°$ C. after the completion of the addition, and continuing the stirring for additional 10 to 180 minutes at that temperature.

Further, water is added dropwise to the thus obtained reaction mixture in order to decompose the tertiary butoxy-substituted phenyl Grignard reagent remaining unreacted therein as well as to wash the reaction product. Then, the organic layer is separated therefrom, and desiccated. Thereafter, the solvent is distilled away therefrom. Thus, the intended tertiary butoxy-substituted triphenylsulfonium salt is obtained.

Besides the above-cited sulfonium salt, diphenyl(4-t-butoxyphenyl) sulfonium triflate and the sulfonium salts used in Examples described hereinafter are specific examples of the present sulfonium salts.

The onium salts of the present invention, although they themselves have low solubility in water, can provide photolysis products having high solubility in water. Accordingly, when used as acid generator of a photoresist, these salts can ensure a great dissolution contrast between the areas irradiated and unirradiated with light. Thus, the present onium salts bring about improvements in resist image characteristics including resolution and focus depth when applied to positive resist materials using poly (hydroxystyrene)'s.

More specifically, the triphenylsulfonium salts in which at least one phenyl group is substituted with a tertiary alkoxy group can readily produce phenol derivatives since the alkoxy substituent therein can be efficiently decomposed by the action of acids produced by photolysis of said salts, thereby achieving a great dissolution contrast. Therefore, the present onium salts can exhibit their excellent effect as acid generator for the positive resist materials of chemical amplification type, and can contribute to the formation of resist images having high resolution and a wide range of focus depth.

The positive resist materials of the present invention are those constituted of three components, (a) a poly (hydroxystyrene) resin in which hydrogen atoms of the hydroxy groups are partly replaced by t-butoxycarbonyl groups, (b) a dissolution inhibitor and (c) an onium salt, with three components (a), (b) and (c) having the weight proportions defined by the relations: $0.55 \leq a$, $0.07 \leq b \leq 0.40$, $0.005 \leq c \leq 0.15$, and $a+b+c=1$, which are developable with an aqueous alkali solution and responsive to high energy radiation.

The onium salt as the foregoing component (c) is any of the present onium salts represented by general formula, $(R)_3S^+M$, already described in detail.

As for the poly(hydroxystyrene) resin in which hydrogen atoms of the hydroxy groups are partly replaced by t-butoxycarbonyl groups, it is desirable that the introduction rate of t-butoxycarbonyl groups be in the range of 10 to 50%. When the introduction rate is not lower than 50%, the solubility of the resin in an aqueous alkali solution is lowered. Therefore, the resulting resist material has lowered sensitivity when developed with a conventional developer. When the introduction rate is below 10%, on the other hand, the resulting resin cannot have a great dissolution-inhibiting effect.

The replacement of the hydrogen atoms in hydroxy groups with t-butoxycarbonyl groups can be effected by a method for protecting functional groups, which is often used in peptide synthesis. Specifically, the protection can be simply performed by reacting a poly(hydroxystyrene) with di-t-butyl dicarbonate in the pyridine solution thereof.

It is desirable that the poly(hydroxystyrene) resin have a weight average molecular weight of at least 10,000 from the viewpoint of the heat resistance of the resist film formed and, what is more, be a monodisperse system with respect to molecular weight distribution from the standpoint of the precision of the pattern formed.

However, when there is used a poly(hydroxystyrene) resin having a broad distribution of molecular weight, such as those prepared by radical polymerization, the resulting resist material involves high molecular weight species which are hard to dissolve in an aqueous alkali solution. These species are responsible for the formed pattern's sloping at the base. To form a high precision pattern, it is therefore advantageous to use a monodisperse poly(hydroxystyrene) resin as prepared by living polymerization.

In accordance with the present invention, a resist material using a poly(hydroxystyrene) obtained by living polymerization (e.g., one which has a molecular weight of 10,000 and a molecular weight distribution of 1.1) can form a 0.2 µm line and space pattern with no sloping at the base and with high precision. Moreover, the formed pattern has satisfactory heat resistance, because no deformation is caused therein by 10 minutes' baking at 150° C.

Using a poly(hydroxystyrene) prepared by radical polymerization(e. g., one which has an average molecular weight of 12,000 and a molecular weight distribution of 3.0), on the other hand, the pattern formed has heat resistance almost equivalent to the above-described case while the sloping at the base is observed even on a 0.5 µm line and space pattern. With this poly(hydroxystyrene), therefore, it is hardly possible to achieve the resolution of 0.2 µm.

Additionally, the term "a monodisperse polymer" as used herein means a polymer which is a monodisperse system in terms of its molecular weight distribution, that is, $1.05 \leq Mw/Mn \leq 1.50$. Herein, Mw stands for the weight average molecular weight of a polymer, and Mn the number average molecular weight.

As for the polymer prepared by living polymerization, its weight average molecular weight can easily be calculated from the weight of the monomer used and the mole number of the polymerization initiator used, or can be determined by a light scattering method. The number average molecular weight thereof can easily be measured with a membrane osmometer.

Further, the molecular weight distribution can be evaluated by Gel Permeation Chromatography (GPC), and the molecular structure can easily be ascertained with the infrared absorption (IR) or $^1$H-NMR spectrum.

A monodisperse resin (or polymer) can be obtained (1) through the fractionation treatment of a product prepared using a radical polymerization method, which thus has a broad molecular weight distribution, or (2) by adopting a living polymerization method. However, the living polymerization method is preferred because the process for rendering the product monodisperse is simple.

Then, the synthesis of a monodisperse poly (hydroxystyrene) resin according to a living polymerization method is illustrated below in detail taking the case of poly(p-hydroxystyrene).

Even if it is attempted to make p-hydroxystyrene monomer undergo living polymerization as it is, the polymerization cannot occur because the hydroxyl group of the monomer reacts with a polymerization initiator. Therefore, there is adopted a method such that a hydroxy-protecting group is introduced into the monomer, the resulting monomer is subjected to living polymerization and then the protecting group is removed from the polymerization product. Thus, the desired p-hydroxystyrene polymer is obtained.

Specific examples of such a protecting group include tertiary butyl, dimethylphenylcarbinyldimethylsilyl, tertiary butoxycarbonyl, tetrahydropyranyl and tertiary butyldimethylsilyl groups.

In the aforementioned living polymerization, it is desirable that an organometallic compound be used as polymerization initiator.

Suitable examples of such an organometallic compound include organic alkali metal compounds such as n-butyl lithium, sec-butyl lithium, t-butyl lithium, sodium naphthalene, sodium anthracene, disodium α-methylstyrene tetramer, cumyl potassium and cumyl cesium.

It is preferable for the living anion polymerization to be carried out in an organic solvent. This organic solvent can be an aromatic hydrocarbon, a cyclic ether or an aliphatic hydrocarbon, with specific examples including benzene, toluene, tetrahydrofuran, dioxane, tetrahydropyran, dimethoxyethane, n-hexane and cyclohexane.

These organic solvents may be used alone or as a mixture of two or more thereof. In particular, it is advantageous to use tetrahydrofuran as the solvent.

The suitable concentration of a monomer in the polymerization reaction is in the range of 1 to 50 wt %, particularly 1 to 30 wt %. The reaction is performed with stirring under high vacuum or in an atmosphere of inert gas such as argon or nitrogen.

The reaction temperature can be chosen freely in a range extending from −100° C. to the boiling point of the organic solvent used. However, it is advantageous to choose the reaction temperature from the range of −78° C. to 0° C. when tetrahydrofuran is used as solvent, while room temperature is preferred as the reaction temperature when benzene is used as solvent.

By the reaction of about 10 minutes' to about 7 hours' duration under a condition as described above, only the vinyl group takes part in the polymerization reaction to produce a desired polymer.

At the point that the desired degree of polymerization has been attained, the polymerization reaction is terminated by adding a terminator such as methanol, water or methyl bromide to the reaction system, thereby obtaining a living polymer having the desired molecular weight.

Further, an appropriate solvent is added to the reaction mixture obtained to yield a precipitate.. The precipitate is washed and dried, thereby purifying and isolating the intended living polymer.

In the living polymerization, 100% of monomer molecules take part in the reaction, so that the yield rate of the polymer produced is approximately 100%. Such being the case, the molecular weight of the living polymer can be adjusted to a desired one by properly controlling the amount of the monomer used and the mole number of the reaction initiator.

The molecular weight distribution of the thus obtained living polymer is monodisperse ($1.05 \leq Mw/Mn \leq 1.50$).

Further, dimethylphenylcarbyldimethylsilyl or t-butyl groups as the protecting groups are removed to obtain poly(p-hydroxystyrene).

The removal of the protecting groups can easily be achieved by dissolving the obtained living polymer in a solvent such as dioxane, acetone, acetonitrile, benzene or a mixture of two or more thereof, and then by adding dropwise an acid such as hydrochloric acid, hydrobromic acid, para-toluenesulfonic acid, etc.

In the above-described removal reaction, the main chain of the polymer is not cleaved, and intermolecular cross-linking reactions do not occur. Accordingly, the poly(p-hydroxystyrene) obtained is still a monodisperse system.

A dissolution inhibitor which can be used as the present component (b) is a material capable of having solubility in an aqueous alkali solution when the resist film is irradiated with high energy beams, such as deep ultraviolet rays, subjected to a thermal treatment, if needed, and then developed with an alkali developer.

Specific examples of such a dissolution inhibitor include t-butoxycarbonyl-protected phenols such as di-t-butoxycarbonylhydroquinone, 4,4'-di-t-butoxycarbonyloxydiphenyl, di-t-butoxycarbonylbisphenol A, di-t-butoxycarbonylbisphenol F, etc.; bile acid derivatives such as cholic acid t-butyl ester, deoxycholic acid t-butyl ester, etc.; and esters protected with tetrahydropyranyl, methoxymethyl, t-butyl, t-amyl or the like, such as 4-t-butoxycarbonylbiphenyl, di-t-butoxyacetylbisphenol A, etc. However, the invention should not be construed as being limited to those examples.

The content of the dissolution inhibitor in the present resist material is desirably in the range of 7 to 40 wt %. When the content is less than 7 wt %, the dissolution inhibiting effect is small; while when it is greater than 40 wt %, the mechanical strength and heat resistance of the resist film decline.

The content of an onium salt in the present resist material is preferably in the range of 0.5 to 15 wt %. When the content is less than 0.5 wt %, the resist material cannot have improved sensitivity; while the contents greater than 15 wt % cause not only an increase in production cost of the resist material but also a decrease in mechanical strength of the resist film.

Forming patterns on a substrate using the present resist materials can be performed with ease in the following manner:

A solution of the present resist material is spin-coated on a substrate, and then prebaked to prepare a coated substrate. The coated substrate is irradiated with high energy beams. Therein, the onium salt (acid generator) in the coating is decomposed to produce an acid. Then, a thermal treatment (PEB) is performed, and thereby is caused the decomposition of the t-butoxycarbonyloxy groups as the produced acid acts as a catalyst. The decomposed groups have no longer the resist dissolution inhibiting effect. As a result of it, a latent image is formed on the substrate. The substrate having the latent image thereon is then developed with an aqueous alkali solution, and rinsed with water to provide a positive-tone pattern.

A reason why the present resist materials have high sensitivities to high energy beams and high resolution is not necessarily clear. However, it can be assumed that (1) the onium salts of the present invention are highly compatible with solvents used in coating resist materials, poly (hydroxystyrene) resins and dissolution inhibitors because of their low solubility in water, thereby ensuring the uniform resist film formation; and (2) since the onium salts are converted to water-soluble compounds and produce acids when irradiated with light and the produced acids decompose the t-butoxycarbonyloxy groups contained in the resins to yield phenolic hydroxy groups, the area irradiated with light comes to have a great dissolution speed in an aqueous alkali solution although the area unirradiated with light retains excellent dissolution inhibiting effect.

In accordance with embodiments of the present invention, the present onium salts which can fulfil their excellent functions as acid generator in chemically amplified positive resists are used in the present positive resist materials. Therefore, the present positive resist materials have high sensitivity to high energy radiation, particularly to deep ultraviolet rays with shorter wavelengths (e.g., KrF excimer laser). Moreover, they have small absorbance in the deep ultraviolet region described above. Further, their plasma etching resistance is high and the resist patterns formed therein have excellent heat-resisting property. Therefore, the present resist materials can form resist images with high resolution and a wide range of focus depth, and they are well suited for fine processing of the substrates used for LSI and the like. In addition, the positive resist materials of the present invention have resist characteristics slightly depending on the time lapsed after irradiation, and require no water in the chemical amplification process. In these respects also, the present resist materials are extremely suitable for the fine processing of substrates for LSI and the like by high energy-radiation lithography.

The present invention will now be described in further detail by reference to the following examples, but it will be understood that the invention is not to be construed as being limited by these examples in any way.

EXAMPLE 1

Onium Salt Synthesis (1):

A solution containing 20.0 g (0.1 mole) of diphenyl sulfoxide in 300 ml of methylene chloride was cooled to −70° C. with a dry ice-methanol bath. Thereto, 23 ml (0.12 mole) of trimethylsilyl triflate was added dropwise with stirring as the temperature of the reaction system was controlled so as not to rise beyond −60° C.

Then, the temperature of the reaction system was changed to 0–5° C. by replacing the dry ice-methanol bath with an ice-water bath, and the reaction was continued for 30 minutes with stirring.

The thus obtained reaction solution was cooled again to −70° C. with a dry ice-methanol bath, and thereto was added dropwise the Grignard reagent prepared from 4.8 g (0.20 mole) of metallic magnesium, 200 ml of tetrahydrofuran and 50.4 g (0.2 mole) of p-t-butoxybromobenzen e according to a conventional method as the reaction temperature was controlled so as not to rise beyond −60° C.

Thereafter, the reaction temperature was changed again to 0–5° C. by replacing the bath with a ice-water bath, and the stirring was continued for additional 30 minutes to finish the reaction.

To the thus obtained reaction mixture was added water in order to decompose the excess Grignard reagent. Thereafter, the resulting solution was washed with 300 ml each of water for three times. The organic layer obtained was dried with anhydrous sodium sulfate, and the solvent was distilled away therefrom. Thus, colorless oily matter was obtained, and it was chromatographed with a silica gel column to isolate the reaction product. The thus obtained product was ascertained to be diphenyl (p-t-butoxyphenyl)sulfonium by the NMR spectral analysis shown below. Additionally, the yield of this product was 24.6 g, and the yield rate was 51.6%.

NMR (CDCL$_3$, δ): 1.28 (9H, s), 7.16 (4H, d), 7.62 (10H, m).

Onium Salt Synthesis (2):

Another reaction product was obtained in the same manner as in the foregoing Synthesis (1), except that p-2-methylpentane-2-yloxybromobenzene was used instead of p-t-butoxybromobenzene.

The product obtained was identified as diphenyl(p-2-methylpentane-2-yloxyphenyl)sulfonium triflate from the NMR spectral analysis shown below. Additionally, the yield rate of this product was 63.6%. NMR (CDCL3,6): 0.92 (3H, t), 1.40 (6H, s), 1.42 (2H, m), 1.73 (2H, m), 7.21 (4H, d), 7.66 (10H, m).

EXAMPLE 2

A resist solution containing the following ingredients:

| | |
|---|---|
| Base resin | 81 parts by weight |
| Di-t-butoxycarbonyl bisphenol A (dissolution inhibitor) | 14 parts by weight |
| Diphenyl (p-t-butoxyphenyl)sulfonium triflate (acid generator, obtained in Onium Salt Synthesis (1)) | 5 parts by weight |
| Ethoxyethyl acetate | 400 parts by weight | was spin-coated onto a silicon substrate at 2,000 rpm, and prebaked on a hot plate at 85° C. for 1 minute. Thus, there was obtained the resist-coated substrate having a resist film thickness of 0.7 μm. The base resin used herein was a poly(p-hydroxystyrene) resin having a t-butoxycarbonyl group-introduction degree of 20 mole %, a molecular weight of 10,000 and a molecular weight distribution (Mw/Mn) of 1.05. After imaging on the coating side of the resist-coated substrate with KrF excimer laser (wavelength: 248 nm), the resist coating was subjected to a heat treatment (PEB) at 85° C. for 2 minutes. The resulting coating was developed with a 2.4% aqueous solution of tetramethylammonium hydroxide (TMAH) for 1 minute, and then rinsed with water for 30 seconds, thereby forming a pattern on the silicon substrate (patterned substrate).

The thus formed pattern on the substrate showed positive-tone characteristics, and the $D_0$ sensitivity of the resist film was 40 mJ/cm$^2$.

When an electron beam having an accelerating voltage of 30 kV was used instead of the foregoing KrF excimer laser, on the other hand, the $D_0$ sensitivity of the resist film was 15.2 μC/cm$^2$.

When imaging was performed with KrF excimer laser, a 0.25 μm line-and-space pattern or hole pattern was resolved, and the pattern formed had almost vertical side walls; while the resolution of 0.2 μm was achieved when the electron beam was used for imaging.

EXAMPLES 3 TO 7

In accordance with the procedures adopted in Example 2, patterned substrates were produced respectively using resist solutions prepared in the same manner as in Example 2, except that the onium salts set forth in Table 1 were used respectively as acid generator in place of p-t-butoxytriphenylsulfonium triflate, and examined for $D_0$ sensitivity and resolution. The thus evaluated $D_0$ sensitivities are shown in Table 2. Additionally, each of the patterns formed herein had resolution equivalent to those achieved in Example 2.

TABLE 1

| Acid Generators used | Symbol |
|---|---|
| Diphenyl(4-t-butoxyphenyl)sulfonium triflate | PAG 1 |
| Diphenyl(4-t-butoxyphenyl)sulfonium tosylate | PAG 2 |
| Diphenyl(4-t-butoxyphenyl)sulfonium hexafluorophosphate | PAG 3 |
| Diphenyl(4-t-butoxyphenyl)sulfonium hexafluoroantimonate | PAG 4 |
| Phenyldi(4-t-butoxyphenyl)sulfonium tosylate | PAG 5 |
| Phenyldi(4-t-butoxyphenyl)sulfonium triflate | PAG 6 |

TABLE 2

| Resist Sample | Acid Generator (represented by Symbol in Table 1) | Electron-Beam Sensitivity (μC/cm$^2$) | KrF Sensitivity (mJ/cm$^2$) |
|---|---|---|---|
| Example 3 | PAG 2 | 3.3 | 72 |
| Example 4 | PAG 3 | 4.2 | 36 |
| Example 5 | PAG 4 | 5.3 | 140 |
| Example 6 | PAG 5 | 2.6 | 75 |
| Example 7 | PAG 6 | 7.2 | 61 |

EXAMPLES 8 TO 22

In accordance with the procedures adopted in Example 2, patterned substrates were produced respectively using resist solutions prepared in the same manner as in Example 2, except that the base resins set forth in Table 3 were used respectively in place of the base resin used in Example 2, the dissolution inhibitors set forth in Table 4 were used respectively in place of the dissolution inhibitor used in Example 2 and the acid generators used in Examples 3 to 7 (set forth in Table 1) were used respectively in place of Diphenyl (p-t-butoxyphenyl)sulfonium triflate, and examined for $D_0$ sensitivity and resolution. The thus evaluated $D_0$ sensitivities are shown in Table 5. Additionally, the resolutions achieved herein were more or less different from one another, but all the line-and-space pattern had the resolution of 0.3 μm. each of the patterns formed herein had resolution equivalent to those achieved in Example 2.

TABLE 3

| Base Resin | Mw | Mw/Mn | Symbol |
|---|---|---|---|
| Poly(hydroxystyrene) | 15,000 | 1.10 | RESIN 1 |
| Poly(hydroxystyrene) whose OH groups are replaced with t-butoxycarbonyloxy groups in a proportion of 30 mole % | 13,000 | 1.13 | RESIN 2 |
| Poly(hydroxystyrene) whose OH groups are replaced with t-butoxycarbonyloxy groups in a proportion of 40 mole % | 50,000 | 1.11 | RESIN 3 |
| Poly(hydroxystyrene) whose OH groups are replaced with tetrahydropyranyloxy groups in a proportion of 25 mole % | 20,000 | 2.00 | RESIN 4 |
| Styrene-hydroxystyrene copolymer (styrene fraction: 20 mole %) | 10,000 | 1.31 | RESIN 5 |

TABLE 4

| Dissolution Inhibitor | Symbol |
|---|---|
| Di-t-butoxycarbonyl bisphenol F | DRI 2 |
| 4,4'-di-t-butoxycarbonyloxybiphenyl | DRI 3 |
| 4,4'-di-t-butoxycarbonylbiphenyl | DRI 4 |
| t-Butyl ester of cholic acid | DRI 5 |
| Di-t-butoxyacetyl bisphenol A | DRI 6 |

TABLE 5

| Resist Sample | Base Resin (represented by Symbol in Table 3) | Dissolution Inhibitor (represented by Symbol in Table 4) | Acid Generator (represented by Symbol in Table 1) | Sensitivity (mJ/cm$^2$) |
|---|---|---|---|---|
| Example 8 | RESIN 1 | DRI 1 | PAG 2 | 42 |
| Example 9 | RESIN 1 | DRI 2 | PAG 2 | 60 |
| Example 10 | RESIN 1 | DRI 3 | PAG 2 | 39 |
| Example 11 | RESIN 1 | DRI 4 | PAG 2 | 100 |
| Example 12 | RESIN 2 | DRI 4 | PAG 2 | 52 |
| Example 13 | RESIN 2 | DRI 5 | PAG 2 | 20 |
| Example 14 | RESIN 2 | DRI 6 | PAG 2 | 33 |
| Example 15 | RESIN 3 | DRI 1 | PAG 2 | 68 |
| Example 16 | RESIN 3 | DRI 1 | PAG 3 | 86 |
| Example 17 | RESIN 3 | DRI 6 | PAG 3 | 150 |
| Example 18 | RESIN 4 | DRI 6 | PAG 4 | 60 |
| Example 19 | RESIN 4 | DRI 5 | PAG 5 | 60 |
| Example 20 | RESIN 4 | DRI 1 | PAG 5 | 43 |
| Example 21 | RESIN 5 | DRI 1 | PAG 6 | 115 |
| Example 22 | RESIN 5 | DRI 2 | PAG 6 | 49 |

What is claimed is:

1. A compound which is diphenyl(4-tert-butoxyphenyl)sulfonium tosylate or phenyldi(4-tert-butoxyphenyl)sulfonium tosylate.

2. A compound of claim 1 which is diphenyl(4-tert-butoxyphenyl)sulfonium tosylate.

3. A compound of claim 1 which is phenyldi(4-tert-butoxyphenyl)sulfonium tosylate.

4. A positive resist composition comprising an onium salt which is diphenyl(4-tert-butoxyphenyl)sulfonium tosylate or phenyldi(4-tert-butoxyphenyl)sulfonium tosylate or a mixture thereof.

5. The composition of claim 4, wherein the composition comprises diphenyl(4-tert-butoxyphenyl)sulfonium tosylate.

6. The composition of claim 4, wherein the composition comprises phenyldi(4-tert-butoxyphenyl)sulfonium tosylate.

7. The composition of claim 4, wherein the composition further comprises a poly(hydroxystyrene) resin in which hydrogen atoms of the hydroxy groups are partly replaced by butoxycarbonyl groups.

8. The composition of claim 7, wherein the composition further comprises a dissolution inhibitor.

9. The composition of claim 7, wherein the poly(hydroxystyrene) resin has 10 to 50% of the hydrogen atoms of the hydroxy groups replaced by butoxycarbonyl groups.

10. The composition of claim 4, wherein the composition further comprises a dissolution inhibitor.

11. The composition of claim 4, wherein the composition contains 0.5 to 15% by weight of the onium salt(s).

* * * * *